(12) United States Patent
Rojas-Wahl et al.

(10) Patent No.: US 7,887,785 B2
(45) Date of Patent: Feb. 15, 2011

(54) PERSONAL CARE COMPOSITIONS WITH ENHANCED PROPERTIES, METHOD OF MANUFACTURE, AND METHOD OF USE THEREOF

(75) Inventors: Roy U. Rojas-Wahl, Teaneck, NJ (US); An-Li Kuo, Chappaqua, NY (US); Suresh K. Rajaraman, Newburg, NY (US)

(73) Assignee: Momentive Performance Materials Inc., Albany, NY (US)

( * ) Notice: Subject to any disclaimer, the term of this patent is extended or adjusted under 35 U.S.C. 154(b) by 1395 days.

(21) Appl. No.: 11/105,750

(22) Filed: Apr. 14, 2005

(65) Prior Publication Data

US 2005/0249690 A1 Nov. 10, 2005

Related U.S. Application Data

(60) Provisional application No. 60/569,725, filed on May 10, 2004.

(51) Int. Cl.
 *A61Q 17/04* (2006.01)
(52) U.S. Cl. .......................... 424/59; 424/60
(58) Field of Classification Search ................... 424/59, 424/60
See application file for complete search history.

(56) References Cited

U.S. PATENT DOCUMENTS

| | | | |
|---|---|---|---|
| 5,008,101 A | 4/1991 | Klimisch et al. ............... 424/59 |
| 5,372,804 A * | 12/1994 | Khoshdel et al. ............... 424/59 |
| 5,540,853 A * | 7/1996 | Trinh et al. ................... 510/101 |
| 5,710,113 A | 1/1998 | Wells et al. |
| 5,770,183 A | 6/1998 | Linares ......................... 424/59 |
| 5,885,558 A | 3/1999 | Stanzl et al. ................... 424/59 |
| 5,904,918 A | 5/1999 | Sterphone et al. ............... 424/69 |
| 6,074,630 A | 6/2000 | Devillez ....................... 424/59 |
| 6,103,221 A | 8/2000 | Arnaud et al. ................. 242/59 |
| 6,197,282 B1 | 3/2001 | Oshima et al. ................. 242/59 |
| 6,284,227 B1 | 9/2001 | Stewart ........................ 424/59 |
| 6,423,306 B2 | 7/2002 | Caes et al. ................. 424/78.02 |
| 6,436,377 B1 | 8/2002 | Hansenne et al. .............. 424/59 |
| 6,517,816 B1 | 2/2003 | Gonzalez ...................... 424/59 |
| 6,558,682 B2 * | 5/2003 | Yen et al. ..................... 424/401 |
| 2002/0022008 A1 | 2/2002 | Forest et al. ................... 424/59 |
| 2002/0031488 A1 | 3/2002 | Kanji et al. ............. 424/70.121 |
| 2004/0042980 A1 | 3/2004 | Kanji et al. ................... 424/59 |
| 2004/0247549 A1 | 12/2004 | Lu et al. |
| 2005/0142079 A1 * | 6/2005 | Garrison et al. ............... 424/59 |

FOREIGN PATENT DOCUMENTS

| | | |
|---|---|---|
| EP | 0555050 | 6/1999 |
| EP | 0920859 | 9/2000 |
| EP | 1 213 006 A | 6/2002 |
| EP | 1281390 | 2/2003 |
| EP | 1371356 | 12/2003 |
| JP | 6122613 | 5/1994 |
| JP | 725727 | 1/1995 |
| WO | WO02/028359 | 11/2002 |
| WO | WO 02/100922 A | 12/2002 |
| WO | WO2004/007592 | 1/2004 |

OTHER PUBLICATIONS

U.S. Appl. No. 60/569,725, filed May 10, 2004, Rojas-Wahl et al.

* cited by examiner

*Primary Examiner*—Margaret G Moore
(74) *Attorney, Agent, or Firm*—Dominick G. Vicari

(57) ABSTRACT

A personal care composition comprising a silicone resin of the generic formula: MQ, wherein the ratio of M to Q is about from 0.01/1 to about 3.96/1; $M_xD_yT_z$, wherein x is about 0.01 to about 3,900,000, y is about 0.035 to about 10,000,000, z is about 0.35 to about 8,000,000; TD, wherein the ratio of T to D is about 0.001/1 to about 73/1; or a combination comprising at least one of the foregoing resins, wherein the resin or resin combination is present in an amount effective to increase the SPF of the formulation at least about 10% over the same formulation without the resin or resin combination. The silicone resins are easily formulated, provide a unique non-tacky sensory experience and exhibit advantageous spreadability while permitting the introduction of additional functional benefits such as homogeneity, better organic compatibility, reduced skin irritation and improved skin feel or shine.

23 Claims, No Drawings

PERSONAL CARE COMPOSITIONS WITH ENHANCED PROPERTIES, METHOD OF MANUFACTURE, AND METHOD OF USE THEREOF

CROSS REFERENCE TO RELATED APPLICATIONS

This application claims the benefit of U.S. Provisional Application Ser. No. 60/569,725, filed May 10, 2004.

BACKGROUND OF INVENTION

This invention relates to personal care compositions, and in particular to personal care compositions that provide enhanced sun protection.

Personal care compositions have a wide range of applications, from sunscreens to cosmetics. Because of their broad use, particularly in sunscreens, it is desirable to provide personal care compositions with improved properties such as enhanced sun protection factor (SPF). In fact, enhanced SPF is of increasing importance in other market segments such as hair care, lipsticks, foundations, mascaras, moisturizers, skin lightening, and anti-aging creams and lotions. Claimed SPFs usually range from 2 to 4 up to 50 to 70.

One of the disadvantages of the current state of the art is that many sunscreens, most notably organic sunscreens, can lead to skin irritation. This skin irritation may be attributable to the active components in those particular applications. Thus, merely increasing the loading of the active components in order to obtain enhanced SPF may be precluded. The Food and Drug Administration imposed upper limits on the amounts of sunscreening agents in personal care applications. Further, certain sunscreening agents need to be precoated or undergo a pre-processing step prior to being used in personal care applications.

There accordingly remains a need in the art for personal care compositions that have enhanced properties in various applications without the increase of active components that can lead to skin irritation. Further, there is a demand in the art for personal care compositions that can be manufactured using materials that does not need to be pre-coated or undergo any other pre-processing step.

BRIEF SUMMARY OF THE INVENTION

The above-described and other deficiencies of the art are met by a personal care composition comprising a silicone resin of the generic formula MQ, wherein the ratio of M to Q is about from 0.01/1 to about 3.96/1;

$M_xD_yT_z$, wherein x is about 0.01 to about 3,900,000, y is about 0.035 to about 10,000,000, z is about 0.35 to about 8,000,000;

TD, wherein the ratio of T to D is about 0.001/1 to about 73/1;

or a combination comprising at least one of the foregoing, wherein the resin or resin combination is present in an amount effective to increase the SPF of the formulation at least about 10% over the same formulation without the resin or resin combination; and further wherein M is of the formula $R^1_aR^2_bR^3_cSiO_{1/2}$ wherein each $R^1$ and $R^2$ is independently a hydroxyl, a halogen, or a monovalent hydrocarbon radical having 1 to about 60 carbon atoms; $R^3$ is a hydroxyl, a halogen, or a monovalent hydrocarbon radical having 1 to about 90 carbon atoms, optionally with a heteroatom, and a=1, 2, or 3; b=0, 1, or 2; c=0, 1, or 2; subject to the limitation that a+b+c=3;

Q is of the generic formula $SiO_{4/2}$;

T is of the formula $R^4SiO_{3/2}$ wherein each $R^4$ is independently a hydroxyl, a halogen, or a monovalent hydrocarbon radical having 1 to about 60 carbon atoms, optionally with heteroatoms;

D is of the formula $R^5R^6SiO_{2/2}$, wherein each $R^5$ and $R^6$ is independently a hydroxyl, a halogen, or a monovalent hydrocarbon radical having 1 to about 60 carbon atoms, optionally with heteroatoms; and a personal care component. The composition of the present invention further provide for a personal care composition wherein the resin or combinations of resin increases the SPF synergistically in combination with the personal care component.

A method of manufacture of the foregoing personal care compositions comprises combining the above-described components.

A method of use of the foregoing personal care compositions comprises applying the composition to an area to be protected from sunlight.

DETAILED DESCRIPTION OF INVENTION

It has unexpectedly been found by the inventors hereof that personal care compositions comprising specific MDTQ resins can be formulated to provide advantageous properties, including enhanced SPF. In addition to SPF enhancement, the resins described herein may result in the improvement of at least one additional property such as easy formulation, non-tackiness, spreadability, homogeneity, organic compatibility, reduced skin irritation, improved skin feel, shine, or combinations comprising at least one of the foregoing properties. The enhancement of any one or more of the foregoing properties may be synergistic. In another advantageous feature, such resins enhance the sun protection factor of cosmetic or personal care formulations when these materials are simply added alone and separately to the formulations, such that no pre-coating or any other pre-processing is necessary.

As is known in the art, MDTQ nomenclature allows silicone resins to be described according to the various monomeric silicone units that make up the polymer. The letter M as used herein denotes the monofunctional unit $R^1_aR^2_bR^3_cSiO_{1/2}$, wherein each $R^1$ and $R^2$ is independently a monovalent hydrocarbon radical having 1 to about 60 carbon atoms, hydroxyl, or a halogen. Each $R^3$ is independently a hydroxyl, a halogen, or a monovalent hydrocarbon radical having 1 to about 90 carbon atoms, optionally with heteroatoms; and a=1-3, b=0-2, and c=0 to 2, provided that the sum of a, b and c is equal to 3. In one embodiment, each $R^1$ and $R^2$ is independently a monovalent hydrocarbon radical having 1 to about 30 carbon atoms, or a halogen and $R^3$ is a hydroxyl, a halogen, or a monovalent hydrocarbon radical having 1 to about 30 carbon atoms, optionally with heteroatoms. In another embodiment, each $R^1$ and $R^2$ is independently a monovalent hydrocarbon radical having 1 to about 15 carbon atoms and $R^3$ is a halogen or a monovalent hydrocarbon radical having 1 to about 30 carbon atoms, optionally with heteroatoms.

As used herein, "hydrocarbon" means a group having carbon-hydrogen bonds, for example alkyl, cycloalkyl, aryl, alkaryl, aralkyl, and the like. The alkyl groups may be further be saturated or unsaturated, linear, branched, or cyclic. Examples of suitable hydrocarbons include alkyl groups such as methyl, ethyl, propyl, isopropyl, butyl, t-butyl, cyclohexyl, cycloheptyl, and octyl; aryl groups such as phenyl and napthyl; alkaryl groups such as xylyl, tolyl, ethylphenyl, isopropylphenyl, n-propylphenyl, n-butylphenyl, isobutyl phenyl, and t-butylphenyl, wherein the alkyl group may be located on any free position on the phenyl ring; aralkyl groups such as benzyl, 1-phenylpropyl, 2-phenylpropyl, 3-phenylpropyl, 1-phenylbutyl, 2-phenylbutyl, 3-phenylbutyl, and 4-phenylbutyl; alkenyl groups such as vinyl, allyl, and cyclohexenyl; alkynyl groups such as propynyl; and the like. As used herein "alkaryl groups" have a point of attachment to the silicon atom on the aryl group, whereas "aralkyl groups" have a point of attachment to the silicon atom on the alkyl group. "Halogen" groups as used herein include fluoro, chloro, bromo, and iodo groups.

The hydrocarbon groups may also be unsubstituted or substituted with one or more groups, such that one or more hydrogens may be replaced with a substituent such a halogen, hydroxyl, oxo, carboxy, thio, alkyl ether, polyether, alkyl ester, amino, amido, or other group having a heteroatom. Specific examples of this type of group are trifluoromethyl, butoxymethyl, and the like. The substituents may themselves be substituted with one or more of the foregoing substituents. Specific examples of this type of group are diisostearoyl propyl and diisostearoyl trimethylolpropane.

The symbol D denotes the difunctional $R^5R^6SiO_{2/2}$, wherein each $R^5$ and $R^6$ is independently a monovalent hydrocarbon radical having 1 to about 60 carbon atoms as described above, optionally with heteroatoms, a hydroxyl or a halogen.

The symbol T denotes the trifunctional unit $R^4SiO_{3/2}$ wherein each $R^4$ is independently a hydroxyl, a halogen, or a monovalent hydrocarbon radical having 1 to about 60 carbon atoms, as described above, optionally with heteroatoms.

The symbol Q denotes the tetrafunctional unit $SiO_{4/2}$ wherein all four oxygens bonded to the silicone atom are bonded to the rest of the polymer. One specific silicone resin that can provide SPF enhancement is an MQ resin wherein M and Q are as defined above, and the ratio of M to Q is about 0.1/1 to about 3.96/1, specifically about 0.5/1 to about 2.5/1 and more specifically about 0.7/1 to about 2/1. The weight average molecular weight of the resin may be about 150 to about 450,000 g/mol, specifically about 2,500 to about 10,000 g/mol and more specifically about 3,500 to about 4,500 g/mol as determined by gas permeation chromatography (GC) or mass spectrometry (MS). Such resins may provide enhanced SPF together with reduced skin irritation.

In a specific embodiment each $R^1$, $R^2$, and $R^3$ is independently an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I. For example, each $R^1$, $R^2$, and $R^3$ is independently any of methyl, ethyl, propyl, isopropyl, butyl, t-butyl, phenyl-1-propyl, phenyl-2-propyl, phenyl-3-butyl, phenyl-4-butyl, 1-phenylpropyl, 2-phenylpropyl, 3-phenylpropyl, 1-phenylbutyl, 2-phenylbutyl, 3-phenylbutyl, isostearoyl propane, diisostearoyl propane, diisostearoyl trimethylolpropane, or fluoro. In one embodiment, $R^1$ and $R^2$ is methyl and $R^3$ is a functionalized alkyl group having about 7 to about 40 carbon atoms. In another embodiment, at least one of $R^1$, $R^2$, and $R^3$ is an aralkyl group or an alkylaryl group having 7 to about 18 carbon atoms, for example n-propylphenyl, isopropylphenyl, n-butylphenyl, t-butylphenyl, 1-phenylpropyl, 2-phenylpropyl, 3-phenylpropyl, 1-phenylbutyl, 2-phenylbutyl, 3-phenylbutyl, or combinations comprising at least one of the foregoing. In still another embodiment, $R^1$ and $R^2$ is methyl and $R^3$ is an aralkyl group having 9 to about 18 carbon atoms, specifically about 9 to about 12 carbon atoms.

The degree of functionalization of the side chains in the MQ resin may be 0.01% to 99.99%. The percentage of silanol groups may be from 0.01 to 99.99 mole percent of the resin and specifically about 0.16 to about 2.5 mole percent of the resin. Such hydroxyl groups may arise due to processing conditions of the specific resin.

In one non-limiting embodiment, the MQ resin may specifically be a solid MQ resin. In another embodiment, the resin is a diisostearoyl trimethylolpropane siloxysilicate having a viscosity of about 400 to about 800 cST. Use of this type of MQ resin is particularly advantageous, in that it allows for the amount of spreading agents to be reduced while still enhancing SPF. Without being bound by theory, it is believed that diisostearoyl trimethylolpropane siloxysilicates dissolve any sunscreening agents.

Suitable MQ resins include trialkylsiloxysilicates such as a trimethoxysilicate available under the trade name SR1000, a mixture of cyclopentasiloxane and trimethylsiloxysilicate available under the trade name SS4230, a mixture of dimethicone and trimethylsiloxysilicate available under the trade name SS4267, a liquid trimethylsiloxysilicate available under the trade name SR399, a diisostearoyl trimethylolpropane siloxysilicate available under the trade name SF 1318, or a phenylpropylsiloxysilicate available under the trade name Silshine151, all of which are available from GE Silicones.

The personal care composition comprising the MQ resin may provide an SPF enhancement, relative to the same composition without the resin, of generally about 10% to about 400%, specifically about 20% to about 300% and more specifically about 30% to about 200%. In one embodiment the SPF may be about 2 to about 100, specifically about 3 to about 90 and more specifically 4 to about 80. Further, the personal care composition comprising the MQ resin may provide reduced skin irritation in a personal care application as well as one or more of the above noted personal care properties. Specifically the personal care composition comprising the MQ resin may advantageously provide for all the noted personal care properties.

In another specific embodiment there is provided a personal care composition comprising a silicone resin of the formula $M_xD_yT_z$ wherein M, D, and T are as defined above, and x is about 0.01 to about 3,900,000, y is about 0.035 to about 10,000,000, and z is about 0.35 to about 8,000,000. This resin may also have a weight average molecular weight of about 150 to about 450,000 g/mole, specifically about 1000 to about 5000 g/mole and more specifically about 3500 to about 4500 g/mole as determined by GPC or MS. The resin may further comprise silanol functionality of about 0.01 to 99.99 mole percent, specifically about 1.5 to about 10 mole percent and more specifically about 1.8 to about 2.3 mole percent of the resin as a result of processing.

More specifically in the formula $M_xD_yT_z$, each $R^1$, $R^2$, $R^3$, $R^4$, $R^5$, and $R^6$ is independently an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I. For example, each $R^1$, $R^2$, $R^3$, $R^4$, $R^5$, and $R^6$ is independently any of methyl, ethyl, propyl, isopropyl, butyl, t-butyl, phenyl-1-propyl, phenyl-2-propyl, phenyl-3-butyl, phenyl-4-butyl, 1-phenylpropyl, 2-phenylpropyl, 3-phenylpropyl, 1-phenylbutyl, 2-phenylbutyl, 3-phenylbutyl, isostearoyl propane, diisostearoyl propane, diisostearoyl trimethylolpropane, or fluoro. In one embodiment, $R^1$, $R^2$, $R^4$, $R^5$, and $R^6$ is methyl and $R^3$ is a functionalized alkyl group having about 7 to about 40 carbon atoms. In another embodiment, at least one of $R^1$, $R^2$, $R^3$, $R^4$, $R^5$, and $R^6$ is an aralkyl group or an alkylaryl group having 7 to about 18 carbon atoms, for example n-propylphenyl, isopropylphenyl, n-butylphenyl, t-butylphenyl, 1-phenylpropyl, 2-phenylpropyl, 3-phenylpropyl, 1-phenylbutyl, 2-phenylbutyl, 3-phenylbutyl, or combinations comprising at least one of the foregoing. In still another embodiment, each $R^1$, $R^2$, $R^4$, $R^5$, and $R^6$ is methyl and $R^3$ is an aralkyl group having 9 to about 18 carbon atoms, specifically about 9 to about 12 carbon atoms.

Exemplary $M_xD_yT_z$ resins are available under the trade name DF581 from GE Silicones. In one non-limiting embodiment, the $M_xD_yT_z$ resin may specifically be a solid $M_xD_yT_z$ resin.

The $M_xD_yT_z$ resin provides an SPF enhancement, relative to the same composition without the resin, of generally about 10% to about 400%, specifically about 20% to about 300% and more specifically about 30% to about 200%. In one embodiment the SPF is about 2 to about 100, specifically about 3 to about 90 and more specifically 4 to about 80. Further, the personal care composition comprising the $M_xD_yT_z$ resin may provide reduced skin irritation in a personal care application as well as one or more of the above noted personal care properties. Specifically the personal care composition comprising the $M_xD_yT_z$ resin may advantageously provide for all the noted personal care properties.

In another specific embodiment there is provided a personal care composition comprising a silicone resin of the generic formula TD, wherein T and D are as defined above, and T and D are present in a ratio of generally about 0.001/1 to about 73/1, specifically about 0.09/1 to about 55/1, and more specifically about 0.1/1 to about 49/1. The TD resin may also have a weight average molecular weight of about 150 to about 450,000 g/mole, specifically about 1000 to about 5000 g/mole and more specifically about 3500 to about 4500 g/mole as determined by GPC or MS. This resin may further comprise silanol functionality of about 0.01 to 99.99 mole percent, specifically about 1.5 to about 10 mole percent and more specifically about 1.8 to about 2.3 mole percent of the resin as a result of processing.

More specifically in the formula TD, each $R^4$, $R^5$, and $R^6$ is independently an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I. For example, each $R^4$, $R^5$, and $R^6$ is independently any of methyl, ethyl, propyl, isopropyl, butyl, t-butyl, phenyl-1-propyl, phenyl-2-propyl, phenyl-3-butyl, phenyl-4-butyl, 1-phenylpropyl, 2-phenylpropyl, 3-phenylpropyl, 1-phenylbutyl, 2-phenylbutyl, 3-phenylbutyl, isostearoyl propane, diisostearoyl propane, diisostearoyl trimethylolpropane, or fluoro. In one embodiment, each $R^5$ and $R^6$ is methyl and $R^4$ and is a functionalized alkyl group having about 7 to about 40 carbon atoms. In another embodiment, at least one of $R^4$, $R^5$, and $R^6$ is an aralkyl group or an alkylaryl group having 7 to about 18 carbon atoms, for example n-propylphenyl, isopropylphenyl, n-butylphenyl, t-butylphenyl, 1-phenylpropyl, 2-phenylpropyl, 3-phenylpropyl, 1-phenylbutyl, 2-phenylbutyl, 3-phenylbutyl, or combinations comprising at least one of the foregoing. In still another embodiment, $R^5$ and $R^6$ is methyl and $R^4$ is an aralkyl group having 9 to about 18 carbon atoms, specifically about 9 to about 12 carbon atoms.

The TD resin provides an SPF enhancement, relative to the same composition without the resin, of generally about 10% to about 400%, specifically about 20% to about 300% and more specifically about 30% to about 200%. In one embodiment the SPF is about 2 to about 100, specifically about 3 to about 90 and more specifically 4 to about 80. Further, the personal care composition comprising the TD resin may provide reduced skin irritation in a personal care application as well as one or more of the above noted personal care properties. Specifically the personal care composition comprising the TD resin may advantageously provide for all the noted personal care properties.

Combinations of the foregoing resins may also be used. MQ resins in combination with at least one of $M_xD_yT_z$ and/or TD resins are of particular utility. The relative amounts of each of the resins are adjusted so as to optimize the personal care characteristics of the personal care compositions, in particular SPF enhancement.

The amount of silicone resin as described above used in the personal care composition will vary depending on the intended use of the composition, the personal care components, the specific resin(s), the desired result, and like considerations, and may be readily determined by one of ordinary skill in the art. The personal care composition may generally contain about 0.001 to about 99 percent by weight (wt. %) of the MQ, $M_xD_yT_z$, and/or TD resins described above, specifically about 0.01 to about 25 wt. % and more specifically about 0.1 to about 15 wt. % and even more specifically about 2 to about 10 wt. % of the total personal care composition. The personal care compositions will further comprise a personal care component, usually more than one, depending on the particular application. Generally the personal care component(s) comprise the balance of the composition, i.e., about 99.99 to about 1 wt. %, specifically about 99.9 to about 75 wt. %, and more specifically about 98 to about 90 wt. % of the total weight of the personal care composition.

Non-limiting examples of personal care components that may be used in the personal care compositions are surfactants, emulsifiers, solvents, emollients, moisturizers, humectants, pigments, colorants, fragrances, biocides, preservatives, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, film formers, thickening agents, particulate fillers, clays, plasticizers, humectants, occlusives, sensory enhancers, esters, other resins and film formers, spherical or other optically active particles including silicon spheres, and the like, and combinations comprising at least one of the foregoing personal care components. Such personal care component(s) may be dispersed, solubilized, or otherwise mixed with the above-described silicone resins.

Preferably, the personal care component(s) do not adversely affect, or substantially adversely affect the SPF enhancement or other desired characteristic of the personal care composition. In one embodiment, the observed SPF enhancement is a result of a synergistic effect arising from a combination of the silicone resin and one or more of the personal care components. Some specific examples of combinations that may produce a synergistic effect are an MQ resin with a emulsifier, preservatives, other sunscreening agents, colorants, pigments, fragrances, active ingredients such as vitamins, alpha-hydroxy acids, beta-hydroxy acids, other hydroxy acids, retinols and their derivatives, niacinamide, skin lightening agents, humectants, occlusives, sensory enhancers, esters, other resins and film formers, spherical or other optically active particles including silicone spheres, as well as other silicones, an emollient, and/or a surfactant; an $M_xD_yT_z$ resin with an emulsifier, preservatives, other sunscreening agents, colorants, pigments, fragrance, active ingredients such as vitamins, alpha-hydroxy acids, beta-hydroxy acids, other hydroxy acids, retinols and their derivatives, niacinamide, skin lightening agents, humectants, occlusives, sensory enhancers, esters, other resins and film formers, spherical or other optically active particles including silicone spheres, as well as other silicones, an emollient, and/or a surfactant; and/or a TD resin with a emulsifier, preservatives, other sunscreening agents, colorants, pigments, fragrances, active ingredients such as vitamins, alpha-hydroxy acids, beta-hydroxy acids, other hydroxy acids, retinols and their derivatives, niacinamide, skin lightening agents, humectants, occlusives, sensory enhancers, esters, other resins and film formers, spherical or other optically active particles including silicon spheres, as well as other silicones, an emollient, and/or a surfactant. More specifically, a synergistic effect may be obtained with an MQ resin with an emulsifier; an MQ resin with an emollient; an MQ resin with a surfactant; an $M_xD_yT_z$ resin with an emulsifier; an $M_xD_yT_z$ resin with an emollient; an $M_xD_yT_z$ resin with a surfactant; a TD resin with an emulsifier; a TD resin with an emollient; andor a TD resin with a surfactant.

The personal care applications where the compositions of the present invention may be used include, but are not limited to, deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations comprising at least one of the foregoing personal care applications.

The particular personal care composition may be used in a variety of product forms depending on the particular application, and may be anhydrous to non-anhydrous, and can encompass, but are not limited to, gels, emulsions, dispersions, sludges, powders, bars, sprays, spritzes, mousses, sticks, balms, foundations and other product forms familiar to those of ordinary skill in the art. They can form single-phases, bi-phases, tri-phases, or can be multiple-phased, lamellar phased, and can form macro-, micro- or nanoemulsions, can form water-in-oil-in-water or oil-in-water-in-oil emulsions, water in silicone emulsions or silicone in oil emulsion, can be simple solids, particles or solutions, as well as other physical forms.

The above-described resins are of particular utility in applications where it is desired to have sunscreen protection, including but not limited to sunscreens, hair care products, cosmetics, skin care products, and the like. As used herein "sunscreen protection" includes protection from any light radiation, including ultraviolet radiation, particularly UVA and UVB. Such protection may be provided by the above-described resins alone or in combination with radiation blocking, absorbing, bending, reflecting or scattering material, henceforth called sunscreening agents, known to persons familiar with the art. The amount of sunscreening agent may vary depending on the particular composition and the SPF level desired, as well as other factors such as regulatory restrictions. In general, the sunscreening agent(s) are present in an amount of up to about 95 wt. % of the total personal care composition, more specifically about 0.01 to about 25 wt. % of the total personal care composition, more specifically about 0.01 to about 15 wt. % of the total personal care composition.

Either blocking or absorbing sunscreening agents may be used. Blocking sunscreening agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreening agents, which are usually organic species, are of special relevance. Such absorbing sunscreening agents include, but are not limited to, UV-A absorbers, which generally absorb radiation in the 320 to 400 nm region of the ultraviolet spectrum, for example anthranilates, benzophenones, and dibenzoyl methanes; and UV-B absorbers, which generally absorb radiation in the 280 to 320 nm region of the ultraviolet spectrum, for example, p-aminobenzoic acid derivatives, camphor derivatives, cinnamates, and salicylates. Specific examples of organic sunscreening agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexylp-methoxycinnamate, 2-ethylhexyl salicylate, glyceryl aminobenzoate, homomenthyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo) benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4,6-tris-(2'-ethylhexyl-1'-oxycarbonyl)-anilinol 1,3,5-triazine, 2-(p-(tert-butylamido)anilinol-4,6-bis-(p-(2'-ethylhexyl 1'-oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden)methylbenzyl acrylamide, 1,4-bisbenzimidazolyl-phenylen-3, 3',5,5'-tetrasulfonic acid and salts thereof, the benzalmalonate-substituted polyorganosiloxanes, the benzotriazole-substituted polyorganosiloxanes (Drometrizole Trisiloxane), solubilized 2,2'-methylene-bis-1,6-(2H-benzotriazol-2-yl)-4-(1,1,3,3-tetramethylbutyl)phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreening agents. In one embodiment, it has been found that a combination of at least three sunscreening agents is effective. In another embodiment it has been found that a combination of four sunscreening agents is effective, especially where chemical sunscreening agents are used.

The personal care composition is specifically formulated for use as a sunscreen, a moisturizer, or a cosmetic. Suitable forms and formulations for such application are known to those of ordinary skill in the art. For example, when formulated for use as a sunscreen, the composition may be in the form of a lamellar emulsion, a mirocoemulsion, or a nanoemulsion. In addition, the emulsions may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets. In one embodiment, the sunscreen application is an emulsion having a continuous aqueous phase, and may be in the form of a stick, a lotion, a gel, a spray, and the like.

Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C) available from GE Silicones, cyclopentasiloxane and dimethicone copolyol (GE SF 1528).

Plasticizers may also be added to the sunscreen formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

In another embodiment there is provided a method of manufacturing the foregoing personal care compositions comprises combining the above-described silicone resin(s) with a personal care component.

A method of use of the foregoing personal care compositions comprises applying the composition to an area to be protected from sunlight.

The disclosed personal care compositions may exhibit a variety of advantages in personal care applications. Some such advantages are SPF enhancement, alone or in combination with sunscreening agents. Other properties of each of the personal care compositions will vary depending on the characteristics of the particular resin(s) chosen, for example the type of resin(s), the type(s) of R groups present, the presence and type(s) of any substitution(s) on the side chains, the molecular weight of the resin(s), and like considerations, as well as the remaining components of the personal care formulation. The desired properties of specific personal care applications may be specifically determined by those skilled in the art. Some specific examples of properties provided by use of the resins herein may include reduced tackiness, enhanced spreadability, homogeneity, enhanced organic compatibility, improved skin feel, improved shine, and/or reduced skin irritation. Test panels may be used to objectively determine the reduced tackiness, homogeneity, organic compatibility and improved skin feel. The enhanced spreadability may be determined by measuring the coefficient of friction in a sample of the personal care composition. Skin irritation may be determined by measuring the onset of erythema. Sunscreens are evaluated according to their ability to slow the erythema or sunburn resulting from the exposure of skin to ultraviolet light. This is accomplished by absorbing damaging radiation before the radiation contacts the skin surface. Measuring the onset of erythema may be an objective measurement as determined by test panels. Shine may be determined by measuring refractive index using a gloss meter.

The following representative examples illustrate the invention and are not to be construed as limiting the claims.

EXAMPLES

A general preparation procedure of the formulations described below was developed. For the organic phase, components were added in the order listed in the tables at 75° C. and at 200 rpm, using a Labmaster Lightning mixer with a propeller blade. The agitation was then increased to 400 rpm while maintaining the temperature at 75° C. The aqueous phase was prepared by taking up EDTA and the carbomer in water, and heating to 75° C. with mixing at 800 rpm until fully dispersed. Then, the water phase was added dropwise to the organic phase at 75° C. and with stirring at 400 rpm. The amine was added to this mixture, which continued to be agitated for another 15 min at 75° C., and was then allowed to cool under continued agitation. When the mixture reached about 40° C., the agitation speed was increased to 500 rpm, and subsequently when 35° C. was reached, the agitation speed was increased to 800 rpm. The products were then agitated at that speed for another 30 minutes. Subsequently, they were homogenized for 5 minutes at 16,000 using an IKA Ultra Turrax T25 homogenizer with a dispersing system (SN-25N/25F from IKA) to form an oil-in-water emulsion.

While SPF is often measured in vivo using the minimal erythemal dose response of human test subjects, some in vitro methods have been developed as well, such as light transmission determination methods. These have been shown to be an acceptable compromise between speed, reproducibility and relevance compared to a typical "in use" application of the sunscreen in every day life. Specifically, an in vitro SPF can be calculated for spectral transmittance at UV wavelengths between 280 and 400 nm according to the equation below:

$$SPF = \left( \int_{280nm}^{400nm} E\lambda \cdot S\lambda \cdot d\lambda \right) \div \left( \int_{280nm}^{400nm} E\lambda \cdot S\lambda \cdot d\lambda \cdot T\lambda \right)$$

where:
E$\lambda$ represents the Commision Internationale de l'Eclairage (CIE) erythemal effectiveness,
S$\lambda$ equates to the solar spectral irradiance; and
T$\lambda$ stands for the measured spectral transmittance determined for each sample.
CIE and S are both functions of wavelength $\lambda$, and their so determined spectra are commonly known to those familiar with the art.

SPF was determined using 2 mg/cm$^2$ of sample on separate quartz plates. A surgical tape manufactured by 3M under the trade name TRANSPORE was employed as a substrate and glued onto the quartz plates. This tape has a rough, semi-transparent topographical surface mimicking the distribution of sunscreen when rubbed-in on human skin. Since it is known that the pore size of the TRANSPORE tape can vary, only tape from a single batch was used in testing. The personal care compositions were spotted at twenty different locations onto the TRANSPORE tape. After an allotted twenty seconds of rub-in time, and a subsequent waiting period of twenty minutes, the SPF was analyzed. Each quartz plate sample was measured with a Labsphere UV-1000S Ultraviolet Transmittance Analyzer at five different locations, using three recordings per location. For each personal care composition tested, a total of eighteen quartz plate samples were measured.

Furthermore, in order to demonstrating the generic nature and substrate-independence of the results disclosed herein, the above SPF determinations were performed using as a substrate a synthetic skin model known to those of ordinary skill in the art as In-Vitro-Skin.

Table 1 sets forth a control oil-in-water formulation and an oil-in water formulation in accordance with the present invention comprising Silshine151 from GE Silicones. Amounts shown are in weight percent.

TABLE 1

| Components | Control Formulation | Silshine151 Formulation |
|---|---|---|
| Stearic Acid | 3.63 | 3.63 |
| Cetyl Alcohol | 0.57 | 0.57 |
| Dimethicone, 350 cSt | 10 | — |
| C$_{12}$-C$_{15}$ Alkylbenzoate | 5 | 5 |
| Caprylic Capric Triglycerides | 5 | 5 |
| Silshine151 (GE Silicones) | — | 10 |
| Octylmethoxycinnamate | 7.5 | 7.5 |
| Octylsalicylate | 5 | 5 |
| Benzophenone-3 | 6 | 6 |
| Butylmethoxydibenzoylmethane | 3 | 3 |
| Tetrasodium EDTA | 0.08 | 0.08 |
| Carbomer | 0.1 | 0.1 |
| Triethanolamine | 1.14 | 1.14 |
| Water (deionized) | 52.97 | 52.97 |
| SPF | 69 | 92 |

When tested as described above using TRANSPORE as a substrate, the control composition gave an average in-vitro SPF of 69, while the Silshine151 personal care composition increased the SPF to 92, an increase of 33%. When tested using the identical formulations with In-Vitro-Skin as a substrate, the control composition gave an average SPF of 45, while the Silshine151 personal care composition enhanced the SPF to 62, an increase of 40%.

Table 2 shows the components of an oil-in-water emulsion using a high load sunscreen and SR1000 (GE Silicones). Amounts shown are in weight percent.

TABLE 2

| Components | Control Formulation | SR1000 Formulation |
|---|---|---|
| Stearic Acid | 3.63 | 3.63 |
| Cetyl Alcohol | 0.57 | 0.57 |
| Dimethicone 350 cSt | 10 | 8 |
| C$_{12}$-C$_{15}$ Alkylbenzoate | 5 | 5 |
| Caprylic Capric Triglycerides | 5 | 5 |
| SR1000 (GE Silicones) | — | 2 |
| Octylmethoxycinnamate | 7.5 | 7.5 |
| Octylsalicylate | 5 | 5 |
| Benzophenone-3 | 6 | 6 |
| Butylmethoxydibenzoylmethane | 3 | 3 |
| Tetrasodium EDTA | 0.08 | 0.08 |
| Carbomer | 0.1 | 0.1 |
| Triethanolamine | 1.14 | 1.14 |
| Water (deionized) | 52.97 | 52.97 |
| SPF | 69 | 91 |

When tested as described above using the TRANSPORE substrate, the control, yielded average SPF of 69. In contrast, substitution of 2 wt. % of dimethicone fluid with SR1000 increased the SPF 32%, to 91.

Table 3 shows the components of an oil-in-water emulsion using a low load sunscreen and Silshine151. Amounts shown are in weight percent.

TABLE 3

| Components | Control Formulation | Silshine151 Formulation |
|---|---|---|
| Stearic Acid | 3.63 | 3.63 |
| Cetyl Alcohol | 0.57 | 0.57 |
| Dimethicone 350 cSt | 10 | — |
| C$_{12}$-C$_{15}$ Alkylbenzoate | 5 | 5 |
| Caprylic Capric Triglycerides | 5 | 5 |
| Silshine151 (GE Silicones) | — | 10 |
| Octylmethoxycinnamate | 3.75 | 3.75 |
| Octylsalicylate | 2.5 | 2.5 |
| Benzophenone-3 | 3 | 3 |
| Butylmethoxydibenzoylmethane | 1.5 | 1.5 |
| Tetrasodium EDTA | 0.08 | 0.08 |

TABLE 3-continued

| Components | Control Formulation | Silshine151 Formulation |
|---|---|---|
| Carbomer | 0.1 | 0.1 |
| Triethanolamine | 1.14 | 1.14 |
| Water, deionized | 63.72 | 63.72 |
| SPF | 26 | 40 |

When tested as described above using the TRANSPORE substrate, the control yielded average in-vitro SPF of 26, while the Silshine151 formulation improved the SPF by 54% to 40.

Table 4 shows a oil-in-water emulsion using a high loading of sunscreen and SF1318. Amounts shown are in weight percent.

TABLE 4

| Components | Control Formulation | SF1318 Formulation |
|---|---|---|
| Stearic Acid | 3.63 | 3.63 |
| Cetyl Alcohol | 0.57 | 0.57 |
| Dimethicone 350 cSt | 10 | 7 |
| $C_{12}$-$C_{15}$ Alkylbenzoate | 5 | 1 |
| Caprylic Capric Triglycerides | 5 | 2 |
| SF 1318 (GE Silicones) | — | 10 |
| Octylmethoxycinnamate | 7.5 | 7.5 |
| Octylsalicylate | 5 | 5 |
| Benzophenone-3 | 6 | 6 |
| Butylmethoxydibenzoylmethane | 3 | 3 |
| Tetrasodium EDTA | 0.08 | 0.08 |
| Carbomer | 0.1 | 0.1 |
| Triethanolamine | 1.14 | 1.14 |
| Water (deionized) | 52.97 | 52.97 |
| SPF | 45 | 59 |

Using In-Vitro-Skin as the substrate, the control composition gave an average in-vitro SPF of 45, while the SF1318 composition increased the SPF by over 31%, to 59. It was further observed that use of SF1318 allowed the amount of spreading agents (the alkylbenzoate and triglycerides), to be reduced while maintaining good spreading and enhancing SPF.

Update Jan. 26, 2005

Additional experimental data supporting SPF enhancement by MQ resins:

TABLE 5

| Components | Control Formulation | SF1318 Formulation |
|---|---|---|
| Cyclopentasiloxane (and) C30-45 Alkyl Cetearyl Dimethicone Crosspolymer, Velvesil 125 (GE Silicones) | 78.25 | 78.25 |
| SF1318 (GE Silicones) | — | 6 |
| Cyclopentasiloxane | 6 | — |
| C12-C15 Alkylbenzoate | 2.50 | 2.50 |
| Caprylic Capric Triglycerides | 2.50 | 2.50 |
| Octylmethoxycinnamate | 3.75 | 3.75 |
| Octylsalicylate | 2.50 | 2.50 |
| Benzophenone-3 | 3.00 | 3.00 |
| Butylmethoxydibenzoylmethane | 1.50 | 1.50 |
| SPF | 35 | 47 |

Using In-Vitro-Skin, the SPF of the control formula of this anhydrous sunscreen gel is 35, while the SF1318 formulation yields an SPF of 47, which represents a 34% increase caused by employing the MQ resin.

TABLE 6

| Components | Control Formulation | SR1000 Caprylyl Methicone Formulation | SR1000 only | Caprylyl Methicone only |
|---|---|---|---|---|
| Stearic Acid | 3.63 | 3.63 | 3.63 | 3.63 |
| Cetyl Alcohol | 0.57 | 0.57 | 0.57 | 0.57 |
| Dimethicone 350 cSt | 10 | 5.00 | 7.50 | 7.50 |
| $C_{12}$-$C_{15}$ Alkylbenzoate | 5 | 5 | 5 | 5 |
| Caprylic Capric Triglycerides | 5 | 5 | 5 | 5 |
| Caprylyl Methicone | — | 2.5 | — | 2.5 |
| SR1000 | — | 2.5 | 2.5 | — |
| TiO2 | 10 | 10 | 10 | 10 |
| Tetrasodium EDTA | 0.08 | 0.08 | 0.08 | 0.08 |
| Carbomer | 0.1 | 0.1 | 0.1 | 0.1 |
| Triethanolamine | 1.14 | 1.14 | 1.14 | 1.14 |
| Water, deionized | 64.47 | 64.47 | 64.47 | 64.47 |
| SPF | 47 | 61 | 58 | 33 |

In this physical sunscreen cream, the SPF enhancing effect of a combination of caprylyl methicone and SR1000 is demonstrated. While the control formulation yields an SPF measured by In-Vitro-Skin of 47, addition of the spreader-resin combination yields an SPF of 61. This represents an increase of 30%. Also, a formulation with Caprylyl Methicone alone exhibits a significant drop in SPF to 33, and while a formulation with SR1000 alone shows significant enhancement to SPF 58, as mentioned, only the combination of SR1000 and Caprylyl Methicone shows the highest SPF, surprisingly pointing towards synergistic effects between the resin and the spreader.

TABLE 7

| Components | Control Formulation | SR1000 & Caprylyl Methicone Formulation | SR1000 only | Capryl Methicone only |
|---|---|---|---|---|
| Stearic Acid | 3.63 | 3.63 | 3.63 | 3.63 |
| Cetyl Alcohol | 0.57 | 0.57 | 0.57 | 0.57 |
| Dimethicone 350 cSt | 10 | 5.00 | 7.50 | 7.50 |
| $C_{12}$-$C_{15}$ Alkylbenzoate | 5 | 5 | 5 | 5 |
| Caprylic Capric Triglycerides | 5 | 5 | 5 | 5 |
| Caprylyl Methicone | — | 2.5 | — | 2.5 |
| SR1000 | — | 2.5 | 2.5 | — |
| Octylmethoxycinnamate | 7.5 | 7.5 | 7.5 | 7.5 |
| Octylsalicylate | 5 | 5 | 5 | 5 |
| Benzophenone-3 | 6 | 6 | 6 | 6 |
| Butylmethoxy-dibenzoylmethane | 3 | 3 | 3 | 3 |
| Tetrasodium EDTA | 0.08 | 0.08 | 0.08 | 0.08 |
| Carbomer | 0.1 | 0.1 | 0.1 | 0.1 |
| Triethanolamine | 1.14 | 1.14 | 1.14 | 1.14 |
| Water, deionized | 52.97 | 52.97 | 52.97 | 52.97 |
| SPF | 65 | 141 | 124 | 44 |

While the control formulation of this sunscreen lotion yields a SPF of 65, the MQ resin and the Caprylyl Methicone formulation yields 141. The formulation with SR1000 alone yields a SPF of 124, while the formulation with Caprylyl Methicone alone yields a SPF of 44. All values were measured using In-Vitro-Skin. Here even more clearly, these data show that even though the MQ resin acts as the predominant SPF enhancer, significant synergies between SR1000 and Caprylyl Methicone exist, especially since the use of Caprylyl Methicone alone leads to lower SPFs compared to the control.

TABLE 8

| Components | Control Formulation | Resin-Spreader 5% | Resin Spreader 10% | MQ alone |
|---|---|---|---|---|
| Cyclopentasiloxane (and) PEG/PPG-20/15 Dimethicone | 2 | 2 | 2 | 2 |
| Sorbitan Oleate | 0.5 | 0.5 | 0.5 | 0.5 |
| Dimethicone 350 cSt | 15.31 | 10.31 | 5.31 | 10.31 |
| Caprylyl Methicone | 2.5 | 5 | 7.5 | 2.5 |
| Bis-Phenylpropyl Dimethicone | 4.31 | 4.31 | 4.31 | 4.31 |
| SR1000 | — | 2.5 | 5 | 5 |
| Octylmethoxycinnamate | 3.75 | 3.75 | 3.75 | 3.75 |
| Octylsalicylate | 2.5 | 2.5 | 2.5 | 2.5 |
| Benzophenone-3 | 3 | 3 | 3 | 3 |
| Propylene Glycol | 1.91 | 1.91 | 1.91 | 1.91 |
| Quaternium-15 | 0.1 | 0.1 | 0.1 | 0.1 |
| Sodium Chloride | 0.57 | 0.57 | 0.57 | 0.57 |
| Water, deionized | 63.55 | 63.55 | 63.55 | 63.55 |
| SPF | 18 | 20 | 24 | 22 |

This example shows that the principle of SPF enhancement by MQ resins works also in water-in-oil emulsions. The control formulation gives a Vitro-Skin SPF of 18, addition of MQ resin SR1000 and the trisiloxane Caprylyl Methicone results in SPFs 20 and 24, respectively, which represents increases of 11% and 33%. Adding SR1000 alone still increases the SPF by 22%. These results show that the broader principle of SPF enhancement by MQ resins also applies to different emulsion systems such as water-in-oil, but they also show the synergistic effects between MQ and the trisiloxane in the resin-spreader combination.

In the above examples, one can measure the percent increase in SPF as it corresponds to the weight percent of silicone resin in the composition. In preferred embodiments the ratio of increase of the SPF value to the weight percent of said silicone resin in the composition can be from 12 to 36 (measured as % SPF increase/wt % silicone resin in the composition). For instance in Example 2, the 32% increase in SPF results in a ratio of 16. In Example 6, the 30% increase in SPF results in a ratio of 12. In Example 7, the 90% increase in SPF results in a ratio of 36.

The singular forms "a", "an", and "the" include plural referents unless the context clearly dictates otherwise. The endpoints of all ranges reciting the same amount or property are independently combinable and inclusive of the recited endpoint. All cited references are incorporated herein by reference.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A personal care composition comprising a formulation including a silicone resin of the generic formula:

MQ, wherein the ratio of M to Q is about from 0.01/1 to about 3.96/1;

$M_xD_yT_z$, wherein x is about 0.01 to about 3,900,000, y is about 0.035 to about 10,000,000, z is about 0.35 to about 8,000,000;

TD, wherein the ratio of T to D is about 0.001/1 to about 73/1;

or a combination comprising at least one of the foregoing resins, wherein the formulation includes a sunscreening agent and has an SPF, wherein the resin or resin combination is present in an amount effective to increase the SPF of the formulation at least about 10% over the same formulation without the resin or resin combination; and further wherein M is of the formula $R^1{}_aR^2{}_bR^3{}_cSiO_{1/2}$ wherein each $R^1$ and $R^2$ is independently the same or different monovalent hydrocarbon radical having 1 to about 60 carbon atoms, a hydroxyl, or a halogen; $R^3$ is a hydroxyl, a halogen, or a monovalent hydrocarbon radical having 1 to about 90 carbon atoms, optionally with a heteroatom; and a=1, 2, or 3; b=0, 1, or 2; c=0, 1, or 2; subject to the limitation that a+b+c=3;

Q is of the generic formula $SiO_{4/2}$;

T is of the formula $R^4SiO_{3/2}$ wherein each $R^4$ is independently a hydroxyl, a halogen, or a monovalent hydrocarbon radical having 1 to about 60 carbon atoms, optionally with heteroatoms;

D is of the formula $R^5R^6SiO_{2/2}$, wherein each $R^5$ and $R^6$ is independently a hydroxyl, a halogen, or a monovalent hydrocarbon radical having 1 to about 60 carbon atoms, optionally with heteroatoms;

a personal care component; and a volatile fluid, said composition achieving an increase in SPF value as compared to the SPF value of a composition without said silicone resin, wherein the ratio of increase of the SPF value to the weight percent of said silicone resin in the composition (% SPF increase/wt. % silicone), is from 12 to 36.

2. The personal care composition of claim 1 wherein the silicone resin is a solid.

3. The personal care composition of claim 1 comprising a silicone resin of the generic formula MQ.

4. The personal care composition of claim 1, wherein each $R^1$, $R^2$, and $R^3$ is independently an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I.

5. The personal care composition of claim 4, wherein $R^1$, $R^2$, and $R^3$ are each independently selected from the group consisting of methyl, ethyl, propyl, isopropyl, butyl, t-butyl, phenyl-1-propyl, phenyl-2-propyl, phenyl-3-butyl, phenyl-4-butyl, 1-phenylpropyl, 2-phenylpropyl, 3-phenylpropyl, 1-phenylbutyl, 2-phenylbutyl, 3-phenylbutyl, isostearoyl propane, diisostearoyl propane, diisostearoyl trimethylolpropane, or fluoro.

6. The personal care composition of claim 1 comprising a silicone resin of the generic formula $M_xD_yT_z$.

7. The personal care composition of claim 6, wherein each $R^1$, $R^2$, $R^3$, $R^4$, $R^5$, and $R^6$ is independently a hydroxyl, an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I.

8. The personal care composition of claim 1 comprising a silicone resin of the generic formula TD.

9. The personal care composition of claim 8, wherein each $R^4$, $R^5$, and $R^6$ is independently a hydroxyl, an alkyl group having 1 to about 8 carbon atoms, an aryl group having 6 to about 18 carbon atoms, an aralkyl having 7 to about 30 carbon atoms, an alkaryl having 7 to about 30 carbon atoms, a substituted alkyl group having about 7 to about 40 carbon atoms, F, Cl, or I.

10. The personal care composition of claim 1 wherein the personal care component is selected from the group consisting of surfactants, emulsifiers, emollients, moisturizers, humectants, pigments, colorants, fragrances, biocides, preservatives, antioxidants, anti-microbial agents, anti-fungal agents, antiperspirant agents, exfoliants, hormones, enzymes, medicinal compounds, vitamins, alpha-hydroxy acids, beta-hydroxy acids, occlusives, salts, electrolytes, alcohols, polyols, absorbing agents for ultraviolet radiation, botanical extracts, organic oils, waxes, film formers, thickening agents, particulate fillers, clays, other silicones, and combinations comprising at least one of the foregoing personal care components.

11. The personal care composition of claim 1, further having easy formulation, non-tackiness, spreadability, homogeneity, organic compatibility, reduced skin irritation, improved skin feel, shine, or combinations comprising at least one of the foregoing properties.

12. The personal care composition of claim 1 where the personal care composition is used in an application selected from the group consisting of deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations comprising at least one of the foregoing applications.

13. The personal care composition of claim 1 where the personal care composition is used in an application selected from the group consisting of sunscreens, cosmetics, hair care products, skin care products and combinations comprising at least one of the foregoing personal care applications.

14. The personal care composition of claim 1, comprising a sunscreening agent selected from the group consisting of cesium oxide, chromium oxide, cobalt oxide, iron oxide, red petrolatum, treated titanium dioxide, titanium dioxide, zinc oxide, and/or zirconium oxide, $BaTiO_3$, $CaTiO_3$, $SrTiO_3$, SiC, p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl diethanolamine p-methoxycinnamate, digalloyl trioleate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N, N-trimethyl-4-(2-oxoborn-3-ylidene methyl) anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4' dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo)benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4,6-tris-(2'-ethylhexyl-1'-oxycarbonyl)-anilinol 1,3,5-triazine, 2-(p-(tert-butylamido)anilinol-4,6-bis-(p-(T-ethylhexyl 1'-oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden)methylbenzyl acrylamide, 1,4-bisbenzimidazolyl-phenylen-3, 3',5,5'-tetrasulfonic acid and salts thereof, the benzalmalonate-substituted polyorganosiloxanes, the benzotriazole-substituted polyorganosiloxanes, solubilized 2,2'-methylene-bis-1,6-(2H-benzotriazol-2-yl)-4-(1,1,3,3-tetramethylbutyl)phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreening agents.

15. The composition of claim 1, wherein the resin or resin combination is present in an amount effective to increase the SPF of the formulation at least about 20 to about 300% over the same formulation without the resin or resin combination.

16. The composition of claim 1, wherein the resin or resin combination is present in an amount effective to increase the SPF of the formulation at least about 30 to about 200% over the same formulation without the resin or resin combination.

17. A method of manufacturing the personal care compositions of claim 1 comprising combining the resin with a personal care component and a sunscreening agent.

18. A method of using the personal care compositions of claim 1 comprising applying the composition to an area to be protected from sunlight.

19. The personal care composition of claim 1 wherein the volatile fluid is water.

20. The personal care composition of claim 1 wherein the silicone resin comprises from 2 to about 10 wt % of the total personal composition.

21. The personal care composition of claim 20 wherein the composition includes at least 52% water based on the total weight of the composition.

22. The personal care composition of claim 21 wherein the increase of SPF of the composition is above 30%.

23. The personal care composition of claim 21 wherein the SPF of the composition is from 91 to 92.

* * * * *